United States Patent
Hale et al.

(10) Patent No.: US 9,746,450 B2
(45) Date of Patent: Aug. 29, 2017

(54) ONLINE GAS CHROMATOGRAPH OPERATION WITH REDUCED USAGE OF CALIBRATION GAS

(71) Applicant: Rosemount Analytical Inc., Houston, TX (US)

(72) Inventors: Shane R. Hale, Jersey Village, TX (US); John R. Beavers, Richmond, TX (US)

(73) Assignee: Rosemount Analytical Inc., Houston, TX (US)

( * ) Notice: Subject to any disclaimer, the term of this patent is extended or adjusted under 35 U.S.C. 154(b) by 35 days.

(21) Appl. No.: 14/498,095

(22) Filed: Sep. 26, 2014

(65) Prior Publication Data
US 2015/0293066 A1    Oct. 15, 2015

Related U.S. Application Data

(60) Provisional application No. 61/979,698, filed on Apr. 15, 2014.

(51) Int. Cl.
*G01N 33/00* (2006.01)
*G01N 30/02* (2006.01)
(Continued)

(52) U.S. Cl.
CPC ..... *G01N 33/0006* (2013.01); *G01N 30/8665* (2013.01); *G01N 2030/025* (2013.01); *G01N 2030/8886* (2013.01)

(58) Field of Classification Search
CPC ............. G01N 30/02; G01N 2030/025; G01N 2030/8886; G01N 30/8665; G01N 33/0006
(Continued)

(56) References Cited

U.S. PATENT DOCUMENTS 3,607,073 A * 9/1971 Stamm ............... G01N 30/8603
422/62
5,545,252 A * 8/1996 Hinshaw ................ G01N 30/32
73/23.25
(Continued)

OTHER PUBLICATIONS

International Search Report and Written Opinion for International Patent Application No. PCT/US2015/024894, date of mailing: Jul. 1, 2015, date of filing: Apr. 8, 2015, 10 pages.
(Continued)

*Primary Examiner* — Daniel S Larkin
(74) *Attorney, Agent, or Firm* — Christopher R. Christenson; Kelly, Holt & Christenson

(57) ABSTRACT

An online gas chromatograph is provided. The online gas chromatograph includes a sample inlet and at least one chromatographic column operably coupled to the sample inlet. At least one valve is interposed between the sample inlet and the at least one chromatographic column. A detector is fluidically coupled to the at least one chromatographic column. A controller is coupled to the detector and to the at least one valve, the controller is configured to control flow from the sample inlet through the chromatograph using the at least one valve. The controller is configured to generate a plurality of sequential calibration cycles, where each calibration cycle has a calibration gas purge operation. The first calibration gas purge operation lasts longer than the second calibration gas purge operation.

8 Claims, 3 Drawing Sheets

(51) Int. Cl.
*G01N 30/86* (2006.01)
*G01N 30/88* (2006.01)

(58) Field of Classification Search
USPC .......................................................... 73/1.02
See application file for complete search history.

(56) References Cited

U.S. PATENT DOCUMENTS

| 5,610,835 | A  | * | 3/1997  | Dominguez | ........... | G01N 30/62 |
|---|---|---|---|---|---|---|
|  |  |  |  |  |  | 436/161 |
| 6,526,811 | B2 | * | 3/2003  | Johnson | ................. | G01N 30/96 |
|  |  |  |  |  |  | 73/1.02 |
| 2013/0134079 | A1 | * | 5/2013  | Jarrell | .................... | B01D 15/14 |
|  |  |  |  |  |  | 210/143 |
| 2013/0304393 | A1 |  | 11/2013 | Sutan |  |  |

OTHER PUBLICATIONS

First Office Action for Chinese Patent Application No. 201510169234.3, dated Aug. 2. 2016, 13 pages.
International Preliminary Report on Patentability for International Patent Application No. PCT/US2015/024894, date of mailing: Oct. 27, 2016, date of filing: Apr. 8, 2015, 7 pages.
Second Chinese Office Action for Chinese Patent Application No. 201510169234.3, dated Mar. 24, 2017, 5 pages including English translation.

* cited by examiner

ONLINE GAS CHROMATOGRAPH OPERATION WITH REDUCED USAGE OF CALIBRATION GAS

CROSS-REFERENCE TO RELATED APPLICATIONS

The present application is based on and claims the benefit of U.S. Provisional Patent application Ser. No. 61/979,698 filed Apr. 15, 2014, the content of which application is hereby incorporated by reference in its entirety.

BACKGROUND

Gas chromatography is the separation of a mixture of chemical compounds due to their migration rates through a chromatographic column. This separates the compounds based on differences in boiling point, polarity, or molecular size. The separated compounds then flow across a suitable detector, such as a thermal conductivity detector (TCD) that determines the concentration of each compound represented in the overall sample. Knowing the concentration of the individual compounds makes it possible to calculate certain physical properties such as BTU or specific gravity using industry-standard equations.

A gas chromatograph is an analyzer that passes a small volume of gas through chromatographic columns to separate and individually measure the unique gas components of the sample mixture. The analysis cycle can be split into two general phases. The first phase is a sample injection phase, and the second phase is the separation and measurement phase. Each analysis cycle requires a certain amount of time to execute depending on the application, typically measured in minutes.

An online gas chromatograph will perform sequential analysis runs of a single or multiple sample streams. After the sample injection phase of the analysis cycle, the next stream gas to be analyzed is then purged through the internal sample flow paths and the sample loop until the end of the analysis cycle to ensure that there is fresh, uncontaminated sample in the sample loop for injection into the columns at the beginning of the next analysis cycle.

A calibration sequence consists of three or more consecutive analysis cycles of calibration gas with a known composition that is used to calculate the individual calibration factors (known as "response factors") for each component measured by the gas chromatograph. In the natural gas transmission market segment where gas chromatographs are used as part of the custody transfer metering system, the gas chromatograph is typically set to automatically calibrate once a day to ensure the accuracy of the measurement, and to validate the correct operation of the analyzer. The calibration gas is typically a custom blended gas that has a certified composition. The cost of the calibration gas can be a significant component of the operating costs of the gas chromatograph. Conserving the amount of calibration gas consumed by gas chromatograph operation would reduce the overall costs of such online gas chromatography.

SUMMARY

An online gas chromatograph is provided. The online gas chromatograph includes a sample inlet and at least one chromatographic column operably coupled to the sample inlet. At least one valve is interposed between the sample inlet and the at least one chromatographic column. A detector is fluidically coupled to the at least one chromatographic column. A controller is coupled to the detector and to the at least one valve, the controller is configured to control flow from the sample inlet through the chromatograph using the at least one valve. The controller is configured to generate a plurality of sequential calibration cycles, where each calibration cycle has a calibration gas purge operation. The first calibration gas purge operation lasts longer than the second calibration gas purge operation.

DETAILED DESCRIPTION OF ILLUSTRATIVE EMBODIMENTS

Figure 1:
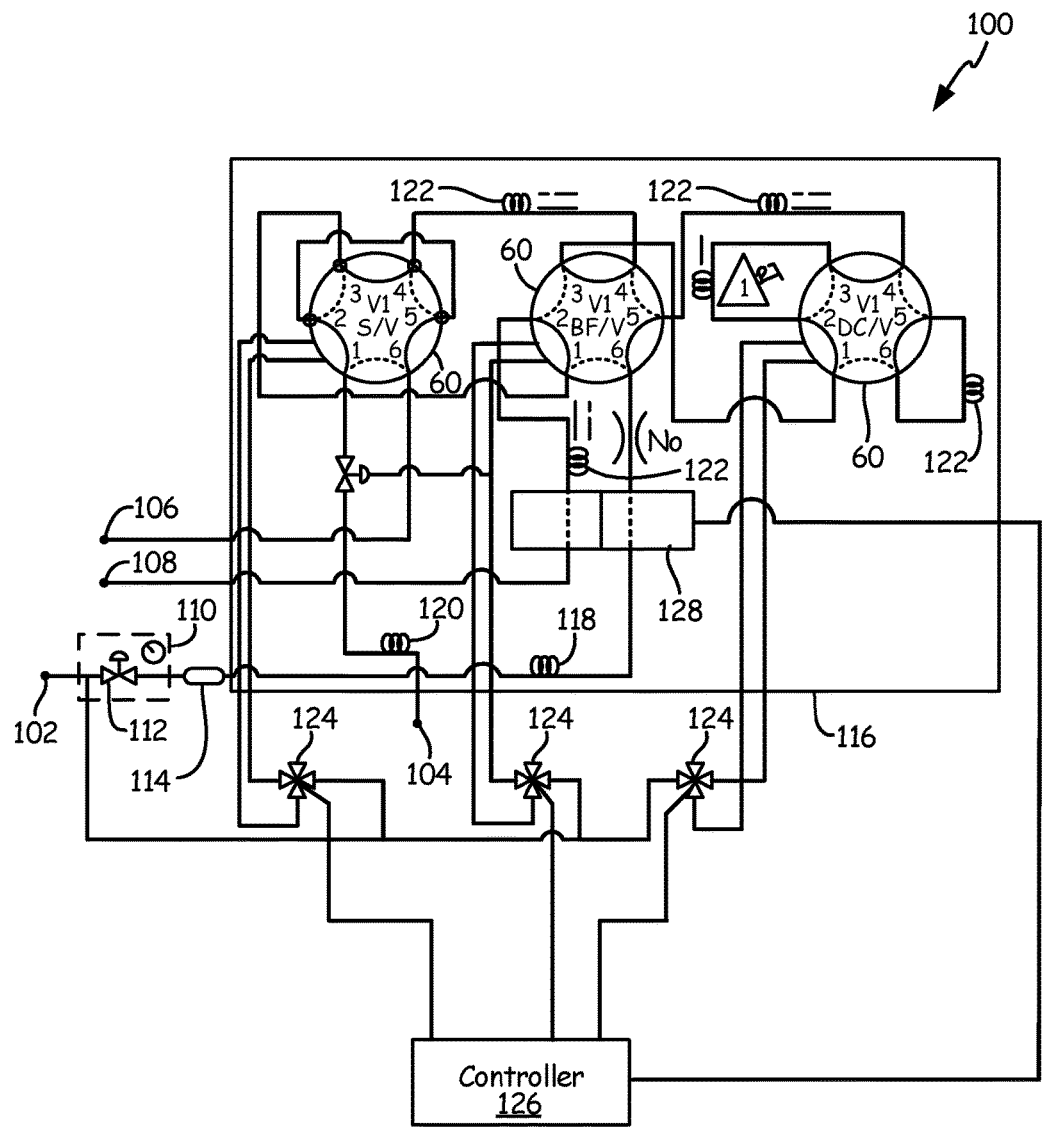
FIG. 1 is a diagrammatic system view of a gas chromatograph with which embodiments of the present invention are particularly useful.

FIG. 1 is a diagrammatic system view of a gas chromatograph with which embodiments of the present invention are particularly useful. Gas chromatograph 100 includes a carrier gas inlet 102, sample inlet 104, sample vent outlet 106 and measure vent outlet 108. Carrier gas is provided to flow panel 110 where it passes through a regulator 112 and dryer 114 before entering analyzer oven 116 and passing through carrier gas pre-heater coil 118. During measurement, sample gas enters chromatograph 100 via sample inlet 104 and passes through sample gas pre-heater coil 120 within analyzer oven 116. During calibration, calibration gas enters sample inlet 104 and passes through sample gas pre-heater coil 120. Both sample gas (during measurement) or calibration gas (during calibration) and carrier gas eventually enter a plurality of pneumatically-controlled multiport selector valves 60 in order to selectively flow various volumes of a sample and/or carrier gas through various chromatographic columns 122 in accordance with known gas chromatography techniques. Each of pneumatically-controlled multiport selector valves 60 is fluidically coupled to a respective solenoid 124 that receives its control signal from controller 126. As shown in FIG. 1, each pneumatically-controlled multiport selector valve 60 has a pair of states. In the first state, the fluidic connections of each valve 60 are shown in solid lines. The fluidic connections of each valve 60 in the second state are shown in phantom. Controller 126 is also operably coupled to detector 128, which is, in one embodiment, a thermal conductivity detector disposed within analyzer oven 116. Thus, controller 126 is able to fully control flow through gas chromatograph 100 by virtue of controlling solenoids 124. Additionally, controller 126 is able to determine the response of detector 128 to gas flow therethrough. In this way, controller 126 is able to selectively introduce the sample into a chromatographic column for a selected amount of time, reverse the flow of gas through the chromatographic column; and direct the reverse flow through the detector to observe and/or record the detector response over time. This provides chromatographic analysis relative to the sample.

Controller 126 preferably includes a microprocessor or other suitable device that is able to execute a sequence of instructions; calculate analytic parameters; and store information. Controller 126 may include, or be coupled to, memory both volatile and nonvolatile.

Figure 2:
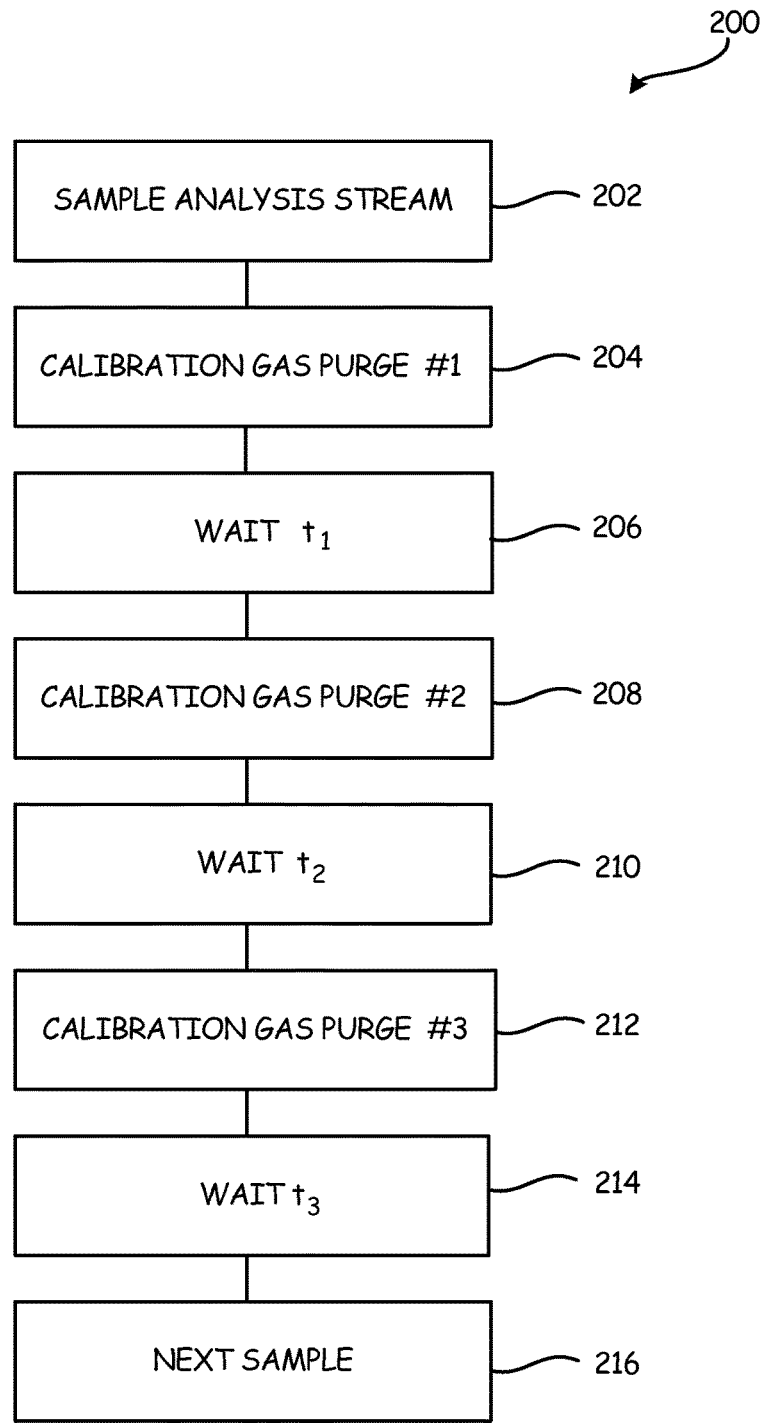
FIG. 2 is a flow diagram of a method of operating an online gas chromatograph in accordance with an embodiment of the present invention.

FIG. 2 is a flow diagram of a method of calibrating an online gas chromatograph in accordance with an embodiment of the present invention. Method 200 begins at block 202 where a sample analysis cycle immediately prior to the first calibration analysis cycle is completed. Upon completion of the sample analysis cycle, control passes to block 204 where calibration gas is purged through the system. During this first calibration gas purge, the system will wait at block 206 until time $t_1$ has elapsed. Time $t_1$, in one embodiment, is a same length of time that is currently used in prior art calibration purge cycles. However, time $t_1$ can be any suitable value that is able to effectively purge calibration gas through the system. Once time $t_1$ has elapsed, method 200 continues at block 208 where a second calibration cycle is executed. During the second calibration cycle, additional calibration gas is purged through the system. However, during the purge of the second calibration gas cycle, the system will wait at block 210 until time $t_2$ has elapsed. In accordance with embodiments of the present invention, time $t_2$ is less than time $t_1$. In this way, less calibration gas is used for the second calibration gas cycle than was used for the first calibration gas cycle. The configured time $t_2$ is selected to significantly reduce the amount of calibration gas that is purged through the sample injection system, while also providing enough purge time to fill the sample loop completely with the calibration gas prior to the injection routine. Next, at block 212, a third calibration cycle is initiated. During the third cycle, calibration gas is purged a third time, and the system will wait time $t_3$, as indicated at block 214, while the calibration gas is purged. Time $t_3$ may be less than, equal to or greater than time $t_2$. However, time $t_3$ is certainly less than time $t_1$. Additionally, as set forth above, time $t_3$ is selected to significantly reduce the amount of calibration gas that is purged through the sample system while also providing enough purge time to fill the sample loop completely with the calibration gas prior to the injection routine. Finally, at block 216, method 200 is complete and the gas chromatograph is ready to analyze the next sample.

Figure 3:
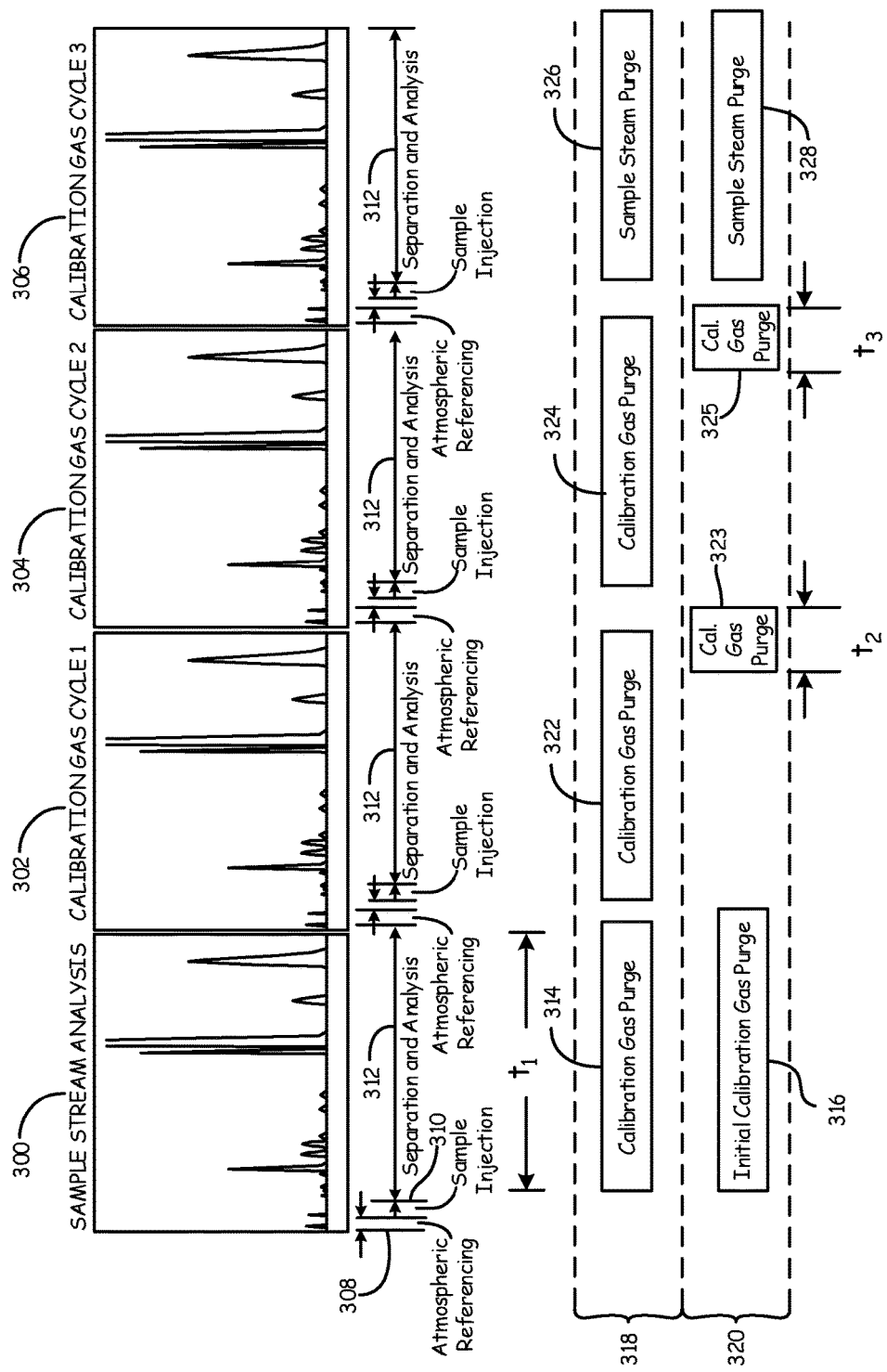
FIG. 3 is a diagrammatic view of sequential calibration gas purge cycles in accordance with an embodiment of the present invention.

FIG. 3 is a calibration gas purge time line illustrating calibration gas purging in accordance with an embodiment of the present invention. As shown in FIG. 3, a sample stream analysis 300 is followed by three subsequent calibration gas cycles 302, 304, and 306. With each cycle, there are two initial steps that are the same. First, atmospheric referencing occurs, as illustrated at reference numeral 308. The atmospheric referencing is then followed by sample injection as illustrated at reference numeral 310. Subsequently, separation and analysis occur as illustrated at reference numerals 312. On the last sample stream analysis prior to a calibration gas cycle, the system is purged with calibration gas. This is illustrated at blocks 314 and 316. Additionally, in order to contrast prior techniques with embodiments of the present invention, region 318 is illustrated above region 320. Region 318 shows calibration gas purges in accordance with prior techniques, while region 320 illustrates calibration gas purges in accordance with embodiments of the present invention. As shown, the initial calibration gas purge prior to calibration gas cycle 302 is substantially the same for embodiments of the present invention in comparison to prior techniques. However, it is the subsequent calibration gas purges where embodiments of the present invention differ from prior techniques. As illustrated, the second calibration gas purge 322 occurring prior to second calibration gas cycle 304 for prior techniques is substantially the same duration as calibration gas purge 314. However, in distinct contrast, the subsequent calibration gas purge 323 for embodiments of the present invention only occurs for time $t_2$ which is substantially less than time $t_1$ for the initial calibration gas purge 316. Similarly, the third calibration gas purge 324 for prior techniques is substantially the same as purges 314 and 322. However, embodiments of the present invention provide a third calibration gas purge 325 with a duration $t_3$ that is also substantially less than time $t_1$. After the third calibration gas cycle 306 is complete, sample stream may be purged into the system in order to measure the next sample, as illustrated at blocks 326 and 328. Additional calibration cycles in excess of the three described may also be configured with the additional calibration cycles also using a shorter purge time than $t_1$.

Embodiments of the present invention are believed to significantly reduce the amount of calibration gas consumed by a gas chromatograph during a typical calibration sequence. A calibration sequence consists of three or more analysis cycles in which purchased high accuracy calibration gas is purged through the system and the sample loop of the analyzer, of which a fixed volume of the gas is injected into the chromatograph columns at the beginning of the analysis cycle. Embodiments of the present invention reduce the amount of calibration gas purged through the system, without compromising the integrity of the sample or the validity of the measurement.

Accordingly, embodiments of the present invention generally solve the problem of consumption of calibration gas by exploiting the fact that after the initial purging of the sample injection system with calibration gas prior to the first analysis cycle in the calibration sequence, the composition of the gas in the sample system will not change for the subsequent cycles of the calibration sequence. Therefore, embodiments of the present invention generally require less purging time and calibration gas volume in order to ensure that a consistent sample is injected into the columns. Additionally, the reduction in calibration gas usage is particularly advantageous for online or process gas chromatographs which are typically not located in a laboratory, but may be located outdoors in a process, such as a refining facility or on a remote transmission pipeline system. In such instance, the calibration gas is provided in the form of a bottle or tank with a fixed volume. Thus, when the calibration gas is depleted, an operator or technician must physically travel to the location of the gas chromatograph and replace the calibration gas container. This process can consume valuable technician time, and may require that the gas chromatograph be taken offline during the calibration gas changeover.

Although the present invention has been described with reference to preferred embodiments, workers skilled in the art will recognize that changes may be made in form and detail without departing from the spirit and scope of the invention.

What is claimed is:

1. An online gas chromatograph comprising:
   a sample inlet configured to receive a sample during a measurement cycle and calibration gas during a calibration cycle;
   at least one chromatographic column operably coupled to the sample inlet;
   at least one valve interposed between the sample inlet and the at least one chromatographic column;
   a detector fluidically coupled to the at least one chromatographic column; and
   a controller coupled to the detector and to the at least one valve, the controller being configured to control flow from the sample inlet through the chromatograph using the at least one valve, wherein the controller is configured to generate a plurality of sequential calibration cycles, each calibration cycle having a calibration gas purge operation and wherein a first calibration gas purge operation lasts longer than a second calibration gas purge operation.

2. The online gas chromatograph of claim 1, wherein the plurality of sequential calibration cycles includes a third calibration cycle having a third calibration gas purge operation, and wherein the first calibration gas purge operation lasts longer than the third calibration gas purge operation.

3. The online gas chromatograph of claim 2, wherein the second calibration gas purge operation takes about the same amount of time as the third calibration gas purge operation.

4. The online gas chromatograph of claim 1, wherein calibration gas purged during the first and second calibration purge gas operations is identical.

5. The online gas chromatograph of claim 4, wherein the calibration gas has a known composition.

6. The online gas chromatograph of claim 5, wherein the calibration gas is a custom blended gas that has a certified composition.

7. The online gas chromatograph of claim 1, wherein the gas chromatograph is located outdoors.

8. The online gas chromatograph of claim 1, wherein the controller is configured to periodically generate the plurality of sequential calibration cycles.

* * * * *